(12) United States Patent
Kurth

(10) Patent No.: US 6,438,399 B1
(45) Date of Patent: Aug. 20, 2002

(54) MULTI-WAVELENGTH FREQUENCY DOMAIN NEAR-INFRARED CEREBRAL OXIMETER

(75) Inventor: Charles D. Kurth, Drexel Hill, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/504,693

(22) Filed: Feb. 16, 2000

Related U.S. Application Data

(60) Provisional application No. 60/120,200, filed on Feb. 16, 1999.

(51) Int. Cl.[7] .................................................. A61B 5/00
(52) U.S. Cl. ........................ 600/323; 600/322; 600/328
(58) Field of Search .................. 600/309–311, 322–324, 600/326–328, 364; 356/39–42

(56) References Cited

U.S. PATENT DOCUMENTS 5,187,672 A * 2/1993 Chance et al. .............. 600/407
5,792,051 A * 8/1998 Chance ...................... 600/310
6,263,221 B1 * 7/2001 Chance et al. .............. 600/310

* cited by examiner

*Primary Examiner*—Eric F. Winakur
*Assistant Examiner*—Matthew J Kremer
(74) *Attorney, Agent, or Firm*—Mathews, Collins, Shepherd & McKay, P.A.

(57) ABSTRACT

The present invention provides a frequency domain near infrared oximeter (fdNIRS) instrument and associated method of determining the oxygenation level of tissue. The tissue is irradiated by a near infrared light source whereby the incident light passing through the tissue is detected by a light detector. Specifically, light signals of a single frequency at at least three separate wavelengths are provided from the near infrared light source. The near infrared light signals are collected with the light detector and, the phase differences between the collected near infrared light signals and a reference near infrared light signal are determined. The fdNIRS oximeter utilizes frequency domain technology to monitor phase shifts relative to a reference signal to derive $SO_2$ through photon transport and Beer-Lambert equations.

7 Claims, 12 Drawing Sheets

| EXPERIMENT | SLOPE | INTERCEPT | $r^2$ |
|---|---|---|---|
| 1 | 1.00±0.09 | 0.3±7.2 | 0.97 |
| 2 | 0.96±0.05 | -3.0±4.2 | 0.99 |
| 3 | 0.97±0.04 | -3.8±3.0 | 0.99 |
| 4 | 1.01±0.09 | -3.3±6.1 | 0.96 |
| 5 | 1.05±0.07 | 0.1±4.5 | 0.99 |
| 6 | 0.97±0.08 | 4.8±5.4 | 0.97 |

FIG. 4.

|  | INFANT (n=8) | CHILD (n=8) | ADULT (n=30) |
|---|---|---|---|
| FRONTAL | | | |
| SCALP | 1±0.5 | 2±1 | 4±2* |
| SKULL | 2±0.5 | 4±1+ | 6±2* |
| CSF | 1±0.3 | 1±0.6 | 2±1* |
| CORTICAL GREY | 9±1 | 10±3 | 12±4 |
| CORTICAL WHITE | 24±2 | 22±6 | 23±6 |
| OCCIPITAL | | | |
| SCALP | 1.6±0.7 | 2±1 | 7±3* |
| SKULL | 4±1 | 6±1+ | 7±3* |
| CSF | 1.3±0.7 | 2±1 | 4±2* |
| CORTICAL GREY | 10±3 | 11±3 | 13±19 |
| CORTICAL WHITE | 12±2 | 17±4 | 12±4 |

Mean±SD. *p<0.05 vs infant and child + p<0.05 vs infant

FIG. 5.

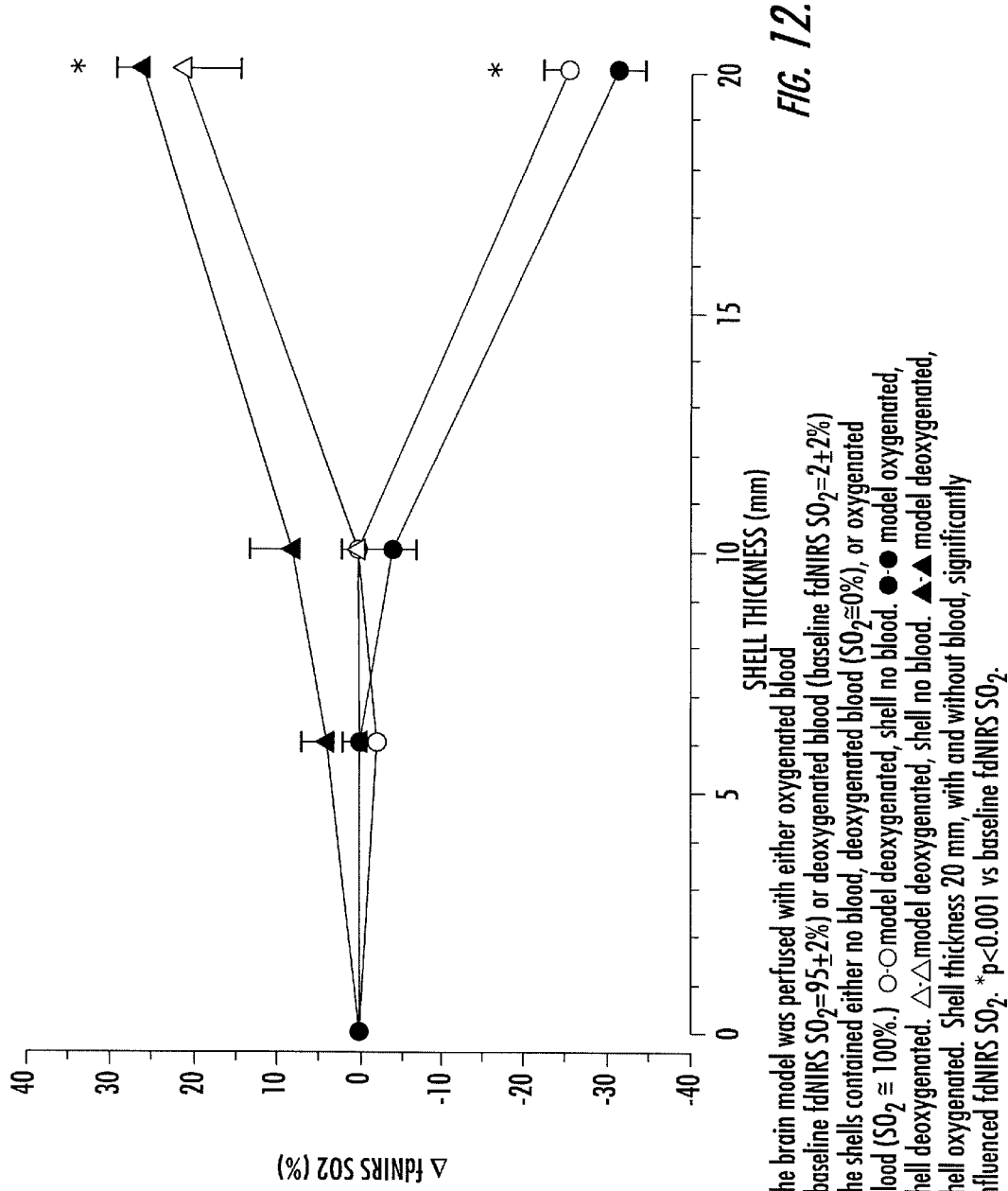

FIG. 12.

The brain model was perfused with either oxygenated blood (baseline fdNIRS $SO_2$=95±2%) or deoxygenated blood (baseline fdNIRS $SO_2$=2±2%) The shells contained either no blood, deoxygenated blood ($SO_2 \cong 0$%), or oxygenated blood ($SO_2 \cong 100$%.) ○-○model deoxygenated, shell no blood. ●-●model oxygenated, shell no blood. △-△model deoxygenated, shell oxygenated. ▲-▲model deoxygenated, shell oxygenated. Shell thickness 20 mm, with and without blood, significantly influenced fdNIRS $SO_2$. *: $p<0.001$ vs baseline fdNIRS $SO_2$.

MULTI-WAVELENGTH FREQUENCY DOMAIN NEAR-INFRARED CEREBRAL OXIMETER

CROSS-REFERENCE TO RELATED APPLICATIONS

This application claims the benefit of U.S. Provisional Application No. 60/120,200, filed Feb. 16, 1999 entitled "Multiwavelength Frequency Domain Near-Infrared cerebral Oximeter".

STATEMENT REGARDING FEDERALLY SPONSORED RESEARCH OR DEVELOPMENT

This invention was supported in part by funds from the U.S. Government (National Institutes of Health contract number N44-NS-5-2314) and the U.S. Government may therefore have certain rights in the invention.

BACKGROUND OF THE INVENTION

Near infrared spectroscopy (NIRS) is a non-invasive, optical technique for monitoring tissue oxygenation. NIRS relies on the relative transparency of tissues to near infrared light (700–900 nm) where oxygenated- and deoxygenated hemoglobin and cytochiome $aa_3$ have distinct absorption spectra. Depending on the instrument, NIRS systems monitor oxygenation as hemoglobin-$O_2$ saturation ($SO_2$), cytoclirome $aa_3$ redox state, or oxy- and deoxy-hemoglobin concentrations. NIRS differs from other oxygenation monitors such as pulse-oxrmetry in that it monitors parenchymal and microcirculatory (eg, capillaries) oxygenation to reflect tissue oxygen supply relative to demand. In clinical medicine, NIRS has been used as a research device to follow cerebral oxygenation during surgery and critical illnesses.

Despite its applicability and availability for several years, NIRS has not been widely utilized in clinical medicine. Uncertainties concerning optical pathlength and light scattering within the tissue have precluded absolute quantitation, limiting NIRS systems to describing relative oxygenation over time. The lack of a standard measure for NIRS has complicated assessment of its accuracy. Because NIRS monitors a tissue field containing capillaries, arteries, and veins, its calculated $SO_2$ represents a mixed vascular $SO_2$. No other method exists at present to measure this mixed vascular $SO_2$. Before NIRS can be evaluated in clinical trials, essential for widespread use, absolute quantitation is required. Several approaches have recently been explored to improve NIRS quantitation. For example, application of radiative transport theory and time or frequency domain spectroscopy permits absolute quantitation through the determination of tissue absorption coefficients ($\mu_a$), eliminating uncertainties in optical pathlength and light scattering. Although absolute quantitation of cerebral $SO_2$ is theoretically possible with time-domain and frequency-domain NIRS (fdNIRS), their accuracy remains untested.

Accordingly, there is a need for NIRS instrument wherein absolute oxygenation levels can be determined quickly and accurately in a clinical setting.

SUMMARY OF THE INVENTION

The present invention comprises a method of determining the oxygenation level of tissue. The tissue is irradiated by a near infrared light source whereby the incident light passing through the tissue is detected by a light detector. Specifically, light signals of a single frequency at at least three separate wavelengths are provided from the near infrared light source. The near infrared light signals are collected with the light detector and, the phase differences between the collected near infrared light signals and a reference near infrared light signal are determined. The phase differences are used to calculate the oxygenation level of the tissue.

In another aspect of the present invention, a method of determining the oxygenation level of tissue comprises irradiating tissue with a near infrared light source, the incident light passing through the tissue to a light detector. Specifically, light signals of a single frequency at three separate wavelengths are provided from the near infrared light source. The near infrared light signals are collected with the light detector and the collected signals define a first, a second, and a third light signal having respective wavelengths $\lambda 1$, $\lambda 2$, and $\lambda 3$. The collected light signals are compared with a reference near infrared signal and the difference in phase between the first and third collected signals $\theta(\lambda 1-\lambda 3)$ is determined. The difference in phase between the second and third collected signals $\theta(\lambda 2-\lambda 3)$ is determined and a phase difference ratio of $\theta(\lambda 1-\lambda 3)/\theta(\lambda 2-\lambda 3)$ is defined. The oxygenation level of the tissue is derived from the phase difference ratio and known tissue absorption constants.

BRIEF DESCRIPTION OF THE SEVERAL VIEWS OF THE DRAWINGS

The foregoing summary as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 4 is a table showing the linear relationships between fdNIRS $SO_2$ and CO-oximeter $SO_2$ in accordance with a preferred embodiment of the present invention;

FIG. 5 is a table of typical ranges of extracranial tissue thickness;

FIG. 12 is a graph of detected oxygenation levels vs. varying brain shell (i.e bone) thickness in accordance with a preferred embodiment of the invention.

DETAILED DESCRIPTION OF THE INVENTION

Certain terminology is used herein for convenience only and is not to be taken as a limitation on the present invention. The term "brain model" is generally defined as any tissue structure. In the supporting examples cited herein, the neonatal brain model was used to demonstrate a particular applicability and to confirm its reliability. The term brain model is not limited to neonatal brains or brain tissue.

Time and frequency domain have been applied to near infrared spectoscopies (NIRS) to determine optical pathlength, light scattering, and absorption. In time-domain spectroscopy, light attenuation is measured as a function of time relative to a pulsed light source, whereas in frequency-domain spectroscopy, light attenuation is measured relative to a light source whose intensity is modulated sinusoidally. The advantages of frequency domain spectroscopy include less expensive and less complex hardware, as well as continuous monitoring capability.

The present invention provides method of determining the oxygenation level of tissue with a frequency domain near infrared spectroscopic (fdNIRS) instrument or "fdNIRS oximeter." The multi-wavelength frequency domain oximeter as described herein utilizes an $SO_2$ algorithm to derive tissue oxygenation. A brain model of an in-vitro neonatal brain is used to demonstrate the accuracy of the oximeter. The brain model is a solid plastic structure containing a vascular network perfused with blood in which hemoglobin oxygen saturation ($SO_2$) was measured by co-oximetry, providing a standard for comparison. The use of NIRS to monitor cerebral oxygenation in adults has been controversial because of concerns of extracranial tissue interference. NIRS monitors the tissue beneath the optical fibers, which includes scalp (skin, subcutaneous fat, muscle), skull, cerebrospinal fluid, and finally, the brain. When the extracranial tissues are thin as in neonates, infants and children, the brain can be monitored from the surface of the head without interference. In adults, the extracranial tissues are thicker and may contaminate the signal and bias the $SO_2$ measurement. (FIG. 5). Data discussed below indicates that at a 4 cm optode separation, the extracranial tissues in adults can bias the measurement as much as 32%. Plastic shells of varying thickness (0.5–2 cm) with a vascular network of their own and encircling the brain model were also added to simulate extracranial tissues of the infant, child, and adult.

Figure 1:
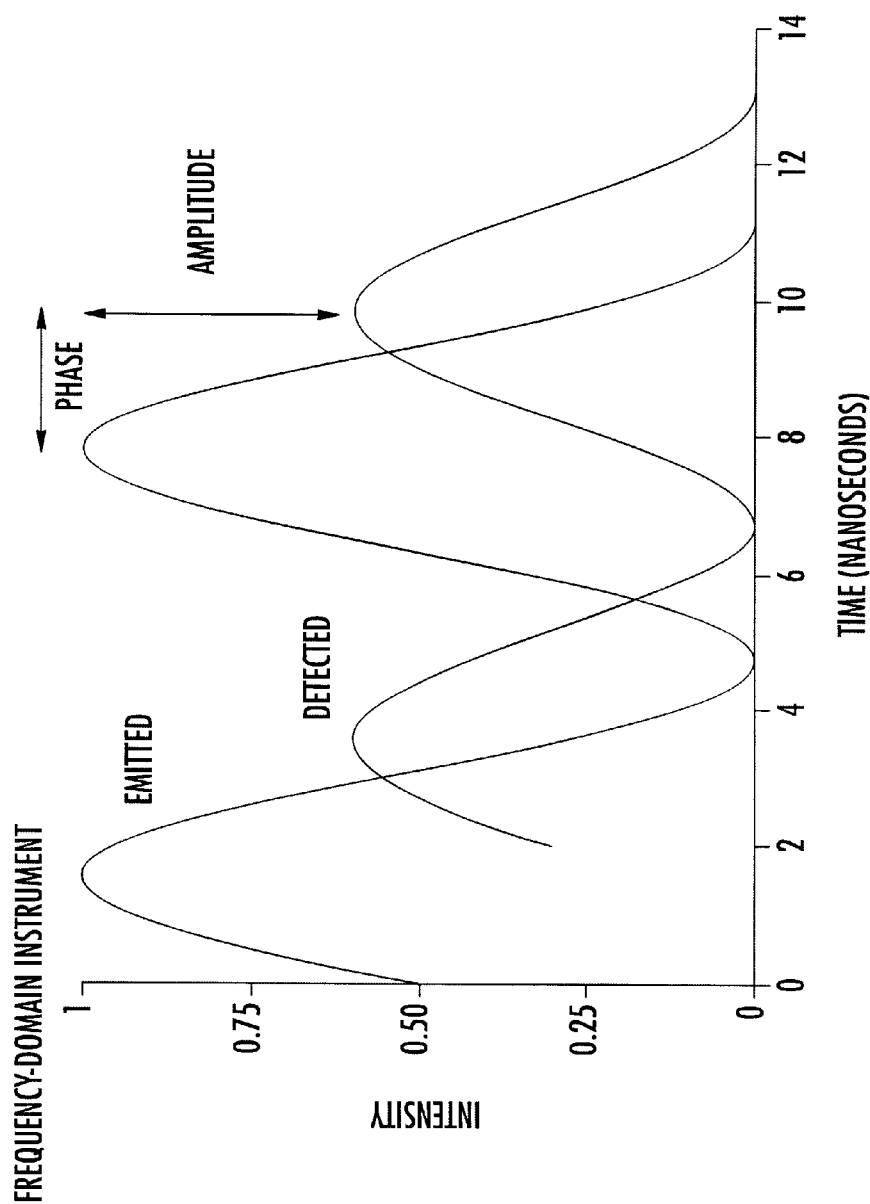
FIG. 1 is a time vs. amplitude graph of emitted and detected signals of a typical prior art frequency domain oximeter.
Figure 2:
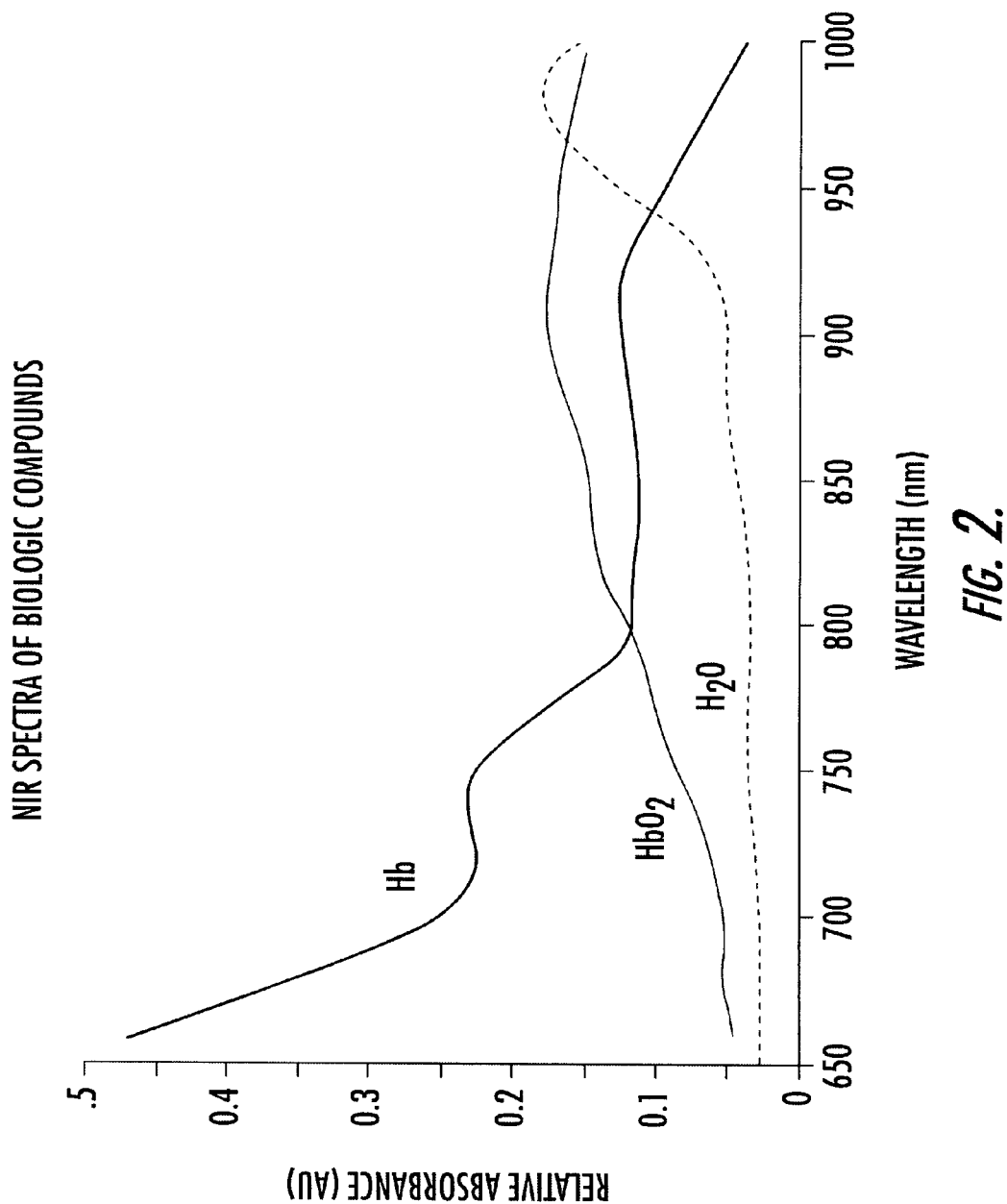
FIG. 2 is an a graph of absorption spectra vs. wavelength graph of Hb, $HbO_2$ and $H_2O$.
Figure 3:
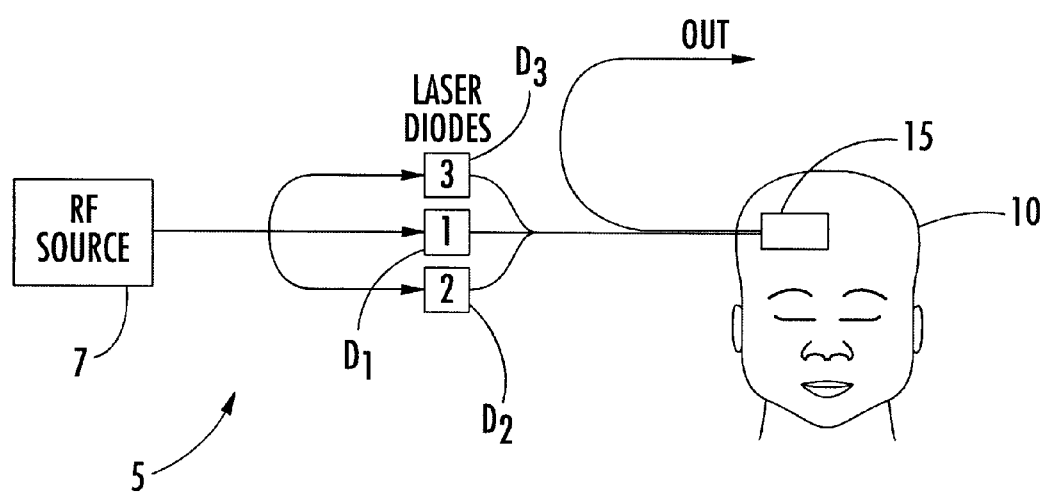
FIG. 3 is a schematic diagram of an oximeter using the frequency domain algorithm in accordance with the preferred embodiment of the invention.

Referring now to FIG. 3, a fdNIRS oximeter 5 is shown (Model PMD 4002, NIM Incorporated, Philadelphia, Pa.). The oximeter 5 is a time-shared 3 wavelength/4-channel design utilizing laser diodes D1–D3 at measuring wavelengths of ($\lambda$1) 754 nm, ($\lambda$2) 785 nm, and ($\lambda$3) 816 nm, with a reference wavelength that is not directed through the brain model 10. The laser light intensities are sinusoidally oscillated at a high frequency, such as 200 MHz (RF source 7). The oximeter 5 employs heterodyne frequency-domain technology to monitor phase-shifts at the three measuring wavelengths relative to an internal reference. A reference mold, is used to calibrate the oximeter 5. Preferably, the laser light is delivered to and from the brain model 10 by 2 fiberoptic bundles, each 1-cm in diameter and 1.8 m in length. The fiberoptic bundle ends are in contact with the brain model 10. In the preferred embodiment, the bundle ends are mounted in soft rubber housing (optical probe 15) and secured circumferentially to the side of the brain model 10. The distance separating the bundle and detector(not shown) in the probe 15 is adjustable to 3 cm, 4 cm, 5 cm, or 6 cm. Light returning to the oximeter 5 is detected with a photomultiplier tube (Model R928, Hamamatsu Photonics, Hamamatsu, Japan, also not shown). The output (OUT) of probe 15 is operably linked to a 4 channel LED display for displaying the AC signal at the corresponding wavelength to indicate signal adequacy. Also, an LCD phase meter is operably linked to the output (OUT) of probe 15 to display the phase difference between the measuring wavelength and the internal phase reference. Preferably, phase angle signals for each wavelength are processed by an analog to digital converter for analysis and storage by a processor (not shown). The processor captures the phase angle signals (4/sec) and the signal average over 15 seconds is recorded during the experiments. The oximeter 5 phase angle signal to noise is ±2% (phase noise ±0.1°, phase drift <0.3°/h). Those skilled in the art recognize that the hardware described above can be separate components or a single probe device performing the collective functions of the components described above. Similarly the method disclosed herein can be performed with a variety of phase shift monitoring and optical devices, it is understood that the specific hardware embodiment disclosed herein is a single illustrative example.

The brain model 10 is constructed of a series of shells. The shells circumscribe an interior of the brain model 10 to simulate brain and extracranial tissues, respectively. The brain model 10 is a plastic cylinder containing a microvascular network perfused with human blood equilibrated with $O_2$, $N_2$, and $CO_2$ in a closed circuit (not shown). The circuit consists of the model brain, bubble oxygenator (Model Bio-2, Baxter Healthcare Inc, Irvine, Calif.), heater-water bath, and a roller pump (Model RS-7800, Renal Systems, Minneapolis, Minn.). The brain's vascular volume comprises 5% of its total volume to simulate normal cerebral blood volume. Diameter of the brain and vascular channels are 10 cm and 974±20 $\mu$m, respectively. Blood $SO_2$ is regulated by adjusting the flow of $O_2$ and $N_2$ in the circuit and measured from an aliquot of blood by CO-Oximetry (Instrumentation Laboratory 282, Lexington, Mass.). Adjusting the quantity of blood and diluent (0.9% NaCl) in the circuit regulates hemoglobin concentration. Blood temperature is adjusted with the water bath jacketing the oxygenator.

The shells encircling the brain model 10 are composed of plastic and contained a microvascular network. The shells fit tightly against the brain model 10. The microvascular network, representing approximately 4% of the shell's total volume, is imbedded in the shell employing the same method as for the brain model 10. After fully oxygenated or deoxygenated blood (obtained from the oxygenator bubbled with $O_2$ or $N_2$) is perfused anaerobically through the shells, the microvascular network is sealed with wax. The shells are constructed of a clear polyester resin (Castin Craft, ETI, Fields Landing, Calif., USA) to which titanium dioxide emulsion (Golden Artist Colors Inc., New Berlin, N.Y., USA) is added to yield a concentration of 0.5%, compared with the 1.2% concentration in the brain model 10, to simulate the lessor light scattering properties of the skull. The thickness of shells is 6 mm, 10 mm, and 20 mm to simulate the thickness of the infant, child, and adult extracranial tissues.

Preliminary studies defined the thickness of the infant, child, and adult extracranial and intracranial tissues. Magnetic resonance images of the head from 8 infants (age 3–10 months), 8 children (age 4–9 years), and 30 adults (age 20–64 years) were reviewed, selected at random from medical records of patients who had normal anatomy, as interpreted by a neuroradiologist for constructing the brain model 10.

I. Measurement Method (Algoritlm Derivation)

The derivation of the algorithm for relating the phase differences of the signals provided by the light source of probe 15 to the detector is explained herein. In the near infrared spectrum, several compounds in biologic tissues contribute to light absorption, including water, oxygenated hemoglobin ($HbO_2$), deoxygenated hemoglobin (Hb), and oxygenated and deoxygenated cytochrome $aa_3$. If the absorption coefficient ($\mu_a$) represents the sum of that contributed by each compound, then expressions may be developed using the Beer-Lambert equation. The Beer-Lambert equation is an algebraic expression relating light behavior to concentration of absorbing compounds.

$$\mu_a(\lambda 1) = \epsilon^{Hb}(\lambda 1)Hb + \epsilon^{HbO2}(\lambda 1)HbO2 + \mu_a^{other}(\lambda 1) \quad (1)$$

$$\mu_a(\lambda 2) = \epsilon^{Hb}(\lambda 2)Hb + \epsilon^{HbO2}(\lambda 2)HbO2 + \mu_a^{other}(\lambda 2) \quad (2)$$

$$\mu_a(\lambda 3) = \epsilon^{Hb}(\lambda 3)Hb + \epsilon^{HbO2}(\lambda 3)HbO2 + \mu_a^{other}(\lambda 3) \quad (3)$$

Where $\epsilon^{Hb}$ and $\epsilon^{HbO2}$ represent the extinction coefficients for Hb and HbO2, $\mu_a^{other}$ the sum of the absorption coefficients of water and cytochrome $aa_3$, and $(\lambda 1)$, $(\lambda 2)$, and $(\lambda 3)$ indicate wavelengths 1, 2, and 3. $SO_2$ is defined by $$SO_2 = 100 * HbO2/H \quad (4)$$

Where H represents total hemoglobin concentration in the tissue, given by $$H = HbO2 + Hb \quad (5)$$

If $\mu_a^{other}$ is constant across the measuring wavelengths ($\mu_a^{other}(\lambda 3 = \lambda 2 = \lambda 1)$), then combining equations 1 through 5 yields $$\mu_a(\lambda 1 - \lambda 3)/\mu_a(\lambda 2 - \lambda 3) = \{\epsilon^{Hb} + SO_2(\epsilon^{HbO2} - \epsilon^{Hb})\}(\lambda 1 - \lambda 3)/\{\epsilon^{Hb} + SO_2(\epsilon^{HbO2} - \epsilon^{Hb})\}(\lambda 2 - \lambda 3) \quad (6)$$

where the notation, $\mu_a(\lambda 1 - \lambda 3)$, represents the difference in the absorption coefficient between wavelengths 1 and 3. Similarly, the notation, $\{\epsilon^{Hb} + SO_2(\epsilon^{HbO2} - \epsilon^{Hb})\}(\lambda 1 - \lambda 3)$ represents the difference in the expression, $\{\epsilon^{Hb} + SO_2(\epsilon^{HbO2} - \epsilon^{Hb})\}$, between wavelengths 1 and 3. If $\lambda 2$ and $\lambda 3$ are selected such that $\epsilon^{Hb}(\lambda 2 - \lambda 3) \gg SO_2(\epsilon^{HbO2} - \epsilon^{Hb})(\lambda 2 - \lambda 3)$, then equation 6 simplifies to $$\mu_a(\lambda 1 - \lambda 3)/\mu_a(\lambda 2 - \lambda 3) = \epsilon^{Hb}(\lambda 1 - \lambda 3)/\epsilon^{Hb}(\lambda 2 - \lambda 3) + SO_2\{\epsilon^{BbO2} - \epsilon^{Hb}\}(\lambda 1 - \lambda 3)/\epsilon^{Hb}(\lambda 2 - \lambda 3) \quad (7)$$

Equation 7 denotes a linear function between the absorption coefficient difference ratio at 3 wavelengths and $SO_2$. For our fdNIRS, wavelengths 1, 2, and 3 are 754 nm, 785 nm, and 816 nm, respectively. Extinction coefficients for Hb and $HbO_2$ at these wavelengths satisfy $\epsilon^{Hb}(\lambda 2 - \lambda 3) \gg SO_2\{\epsilon^{HbO2} - \epsilon^{Hb}\}(\lambda 2 - \lambda 3)$. For example, $\epsilon^{Hb}(\lambda 2 - \lambda 3)$ is 55 $\mu M^{-1}$ $cm^{-1}$, whereas $SO_2\{\epsilon^{HbO2} - \epsilon^{Hb}\}(\lambda 2 - \lambda 3)$ is $-95$ $\mu M^{-1}$ $cm^{-1}$ at $SO_2$ 1% and $-9500$ $\mu M^{-1}$ $cm^{-1}$ at $SO_2$ 100%.

Several mathematical models exist to recover tissue absorption coefficients. In the radiative-transport model, photon migration through tissue is treated as a difflusional process analogous to heat transfer in an object. The radiative transport model is a complex integro-differential equation. The diffusion approximation is used to solve this equation. Although this approach generally requires an iterative solution, analytical solutions exist for some conditions. The advantage of the analytical solution includes minimal computation time to permit continuous, real-time oximetry. The disadvantage stems from computation errors if the analytical assumptions are incorrect. The results provided herein point to the general adequacy of the radiative transport model assumptions.

The diffusion equation describes the photon fluence rate, $\Phi(r,t)$, or the effective concentration of photons at position (r) and time (t) in the tissue from a light source (S)

$$(1/c) \, \partial/\partial t \Phi(r,t) D \nabla^2 \Phi(r,t) + \mu_a(r,t) = S(r,t) \quad (8)$$

where D is the diffusion coefficient and c is the speed of light. The diffIusion coefficient is given by $$D = 1/(3\,\mu'_s) \quad (9)$$

where $\mu'_s$ is the reduced scattering coefficient of the tissue. The fluence rate within a tissue volume depends non-linearly on the absorption and scattering coefficients of the tissue, such that fluence rate is specified as $\Phi(r, t, \mu_a \mu'_s)$. Temporal reflectance, $R(\rho,t)$, corresponds to the photon current density remitted from the surface of a scattering semi-infinite medium at distance ($\rho$) from the source following impulses of light.

$$R(\rho,t) = (4\,\pi Dc)^{-3/2} \mu'_s{}^{-1} t^{5/2} \exp(-\mu_a ct) \exp(-\rho^2/4Dct) \quad (10)$$

In frequency domain spectroscopy, the light source consists of intensity-modulated light rather than impulses of light. The intensity is sinusoidally modulated at a frequency (f). The detected light intensity a distance ($\rho$) away from the source is both amplitude demodulated (M) and phase-shifted ($\theta$) with respect to the source intensity. Expressions were developed for $\theta$ from the sine and cosine Fourier transforms of equation 10.

$$\theta(\rho,f) = -\Psi \sin(\Theta/2) - \tan^{-1}\{[-\Psi \sin(\Theta/2)/[1+\Psi \cos(\Theta/2)]\} \quad (11)$$

Where $$\Psi = \{\{3\,\mu'_s \rho^2 [(\mu_a c)^2 + (2\,\pi f)^2]^{1/2} c^{-1}\}^{1/2} \quad (12)$$

And $$\Theta = \tan^{-1}\{2\,\pi f/\mu_a c\} \quad (13)$$

In an appropriate scattering and absorbing medium, light source frequency, and emitter-detector separation (eg, 6 $\pi \mu'_s \rho^2 f \gg c$ and $2\,\pi f \gg \mu_a c$), it is possible to reduce equation 11 to $$\theta = (6\,\pi/c)^{1/2} \sin(\pi/4) \rho (\mu'_s f)^{1/2} [1 - \mu_a c/4\,\pi f] \quad (14)$$

In the present invention, $\mu'_s$, $\mu_a$, $\rho$, and f are approximately 7 $cm^{-1}$, 0.10 $cm^{-1}$, 5 cm, and 200 MHz, respectively. Although $2\,\pi f \gg \mu_a$ is not fully satisfied, equation 14 has been shown experimentally to hold for these conditions. Accordingly, an expression can be developed for $\theta$ at 3 wavelengths.

$$\theta(\lambda 1) = (6\,\pi c)^{1/2} \sin(\pi/4)\,\rho[\mu'_s(\lambda 1)f]^{1/2}[1 - \mu'_s(\lambda 1)c/4\,\pi f] \quad (15)$$

$$\theta(\lambda 1) = (6\,\pi c)^{1/2} \sin(\pi/4)\,\rho[\mu'_s(\lambda 2)f]^{1/2}[1 - \mu'_s(\lambda 2)c/4\,\pi f] \quad (16)$$

$$\theta(\lambda 1) = (6\,\pi c)^{1/2} \sin(\pi/4)\,\rho[\mu'_s(\lambda 3)f]^{1/2}[1 - \mu'_s(\lambda 3)c/4\,\pi f] \quad (17)$$

If light scattering is wavelength independent ($\mu'_s(\lambda 1 = \lambda 2 = \lambda 3)$), equations 15–17 can be solved to yield $$\theta(\lambda 1-\lambda 3)/\theta(\lambda 2-\lambda 3)=\mu_a(\lambda 1-\lambda 3)/\mu_a(\lambda 2-\lambda 3) \quad (18)$$

Thus, the absorption coefficient difference ratio is given by the phase difference ratio at 3 wavelengths. $SO_2$ can be calculated from the combination of equation 7 and 18

$$\theta(\lambda 1-\lambda 3)/\theta(\lambda 2-\lambda 3)=\epsilon^{Hb}(\lambda 1-\lambda 3)/\epsilon^{Hb}(\lambda 2-\lambda 3)+SO^2\{\epsilon^{HbO2}-\epsilon^{Hb}\}(\lambda 1-\lambda 3)/\epsilon^{Hb}(\lambda 2-\lambda 3) \quad (19)$$

Equation 19 linearly relates the phase angle difference ratio at 3 wavelengths to $SO_2$.

The extinction coefficients of oxy- and deoxy- hemoglobin at 3 wavelengths (equation 7) are constants that have been determined previously, the wavelengths are selected to satisfy the assumption to derive equation 7. The wavelength independence of absorption by nonhemoglobin compounds (equation 6) and of light scattering (equation 18) are assumed. In-vitro data justify these assumptions. The nonhemoglobin compounds in the brain model were water, plastic, and titanium dioxide (cytochromes were not present). The absorption spectra of these compounds are flat between our measuring wavelengths (754–816 nm) to satisfy equation 6. For in-vivo application, fdNIRS oximetry should not be affected by cytochrome $aa_3$ even though its absorption spectra is not flat, because its absorption is greatly overshadowed by hemoglobin. Light scattering in the brain model 10 arises from red blood cells and titanium dioxide and is wavelength independent from 670 to 830 nm to satisfy equation 18.

II. Experimental Data

Example tests were performed to verify equation 19 and develop an algorithm for the fdNIRS oximeter to calculate $SO_2$, then test prospectively the accuracy of the algorithm. These experiments examined bias, precision, and linear regression of fdNIRS relative to CO-Oximetry; repeatability of fdNIRS; and the effect of fdNIRS source-detector separation, blood temperature, hemoglobin concentration, and shell thickness on fdNIRS $SO_2$.

The fdNIRS optical probe 15 was secured against the side of the brain model 10, emitter and detector 4 cm apart (shells were not present). In the first example, the oxygenator receives nitrogen to deoxygenate the blood perfusing in the brain model 10. fdNIRS phase signals (θ) were recorded at each wavelength as oxygen was added incrementally to increase perfusate oxygen saturation by approximately 5% increments. Perfusate total hemoglobin concentration was constant (15 g/dl). To test equation 19, the phase difference ratio ($[\theta(\lambda 1-\lambda 3)]/[\theta(\lambda 2-\lambda 3)]$) is plotted against perfusate $SO_2$ and an algorithm is developed based on this relationship. In the next 6 experiments, the algorithm was prospectively examined, in which fdNIRS $SO_2$ was compared with CO-oximetry $SO_2$ of the perfusate. The flows of $O_2$ and $N_2$ to the oxygenator are adjusted to achieve 5 levels of perfusate $SO_2$: 0–10%, 20–35%, 45–60%, 70–85%, and 95–100%. The order of the levels is selected at random. Perfusate total hemoglobin concentration is constant during each experiment, varying between 14–16 g/dl among experiments.

Figure 6:
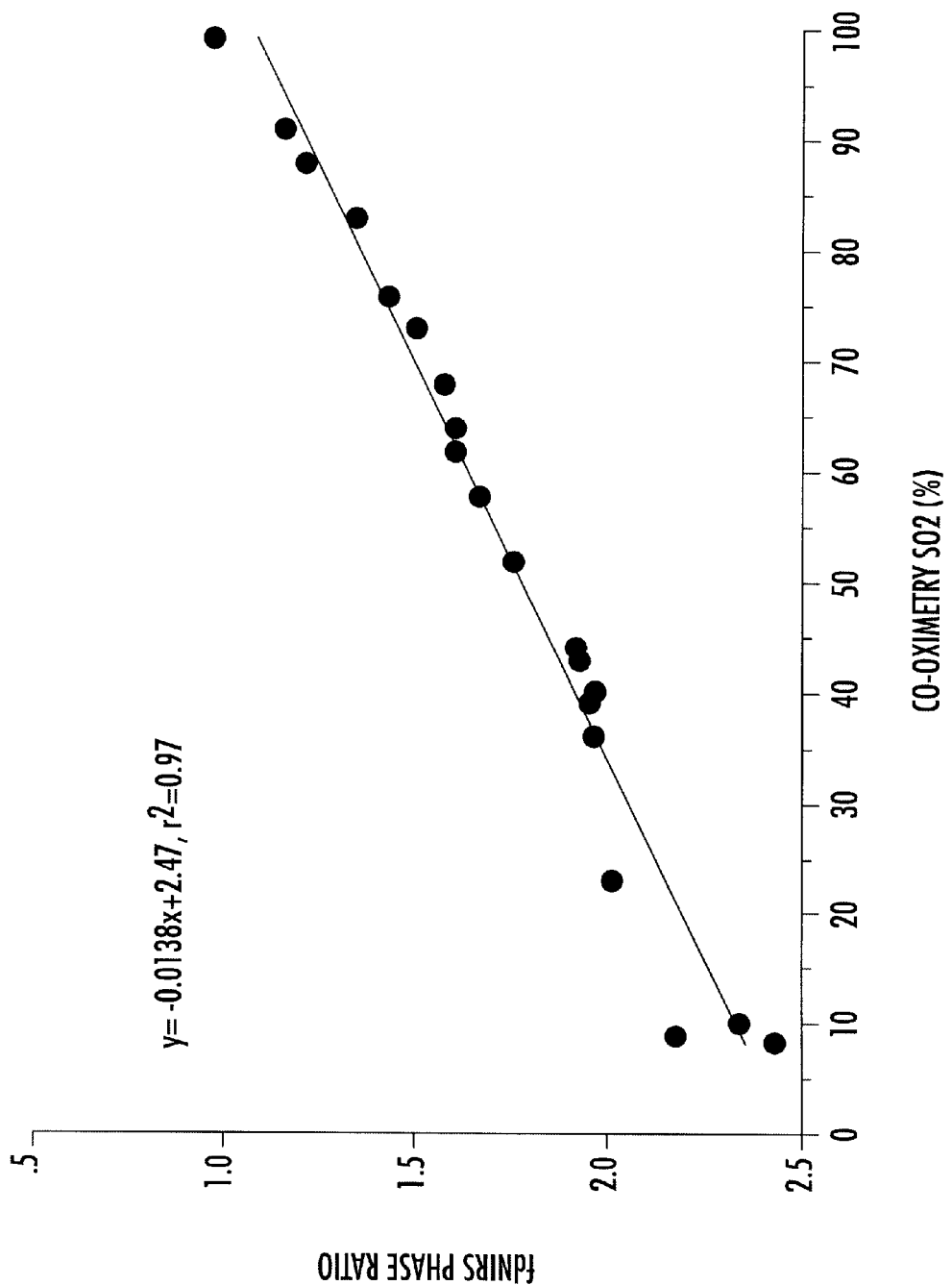
FIG. 6 is a graph of oxygen saturation ($SO_2$) vs. phase difference ratio in accordance with a preferred embodiment of the invention.
Figure 7:
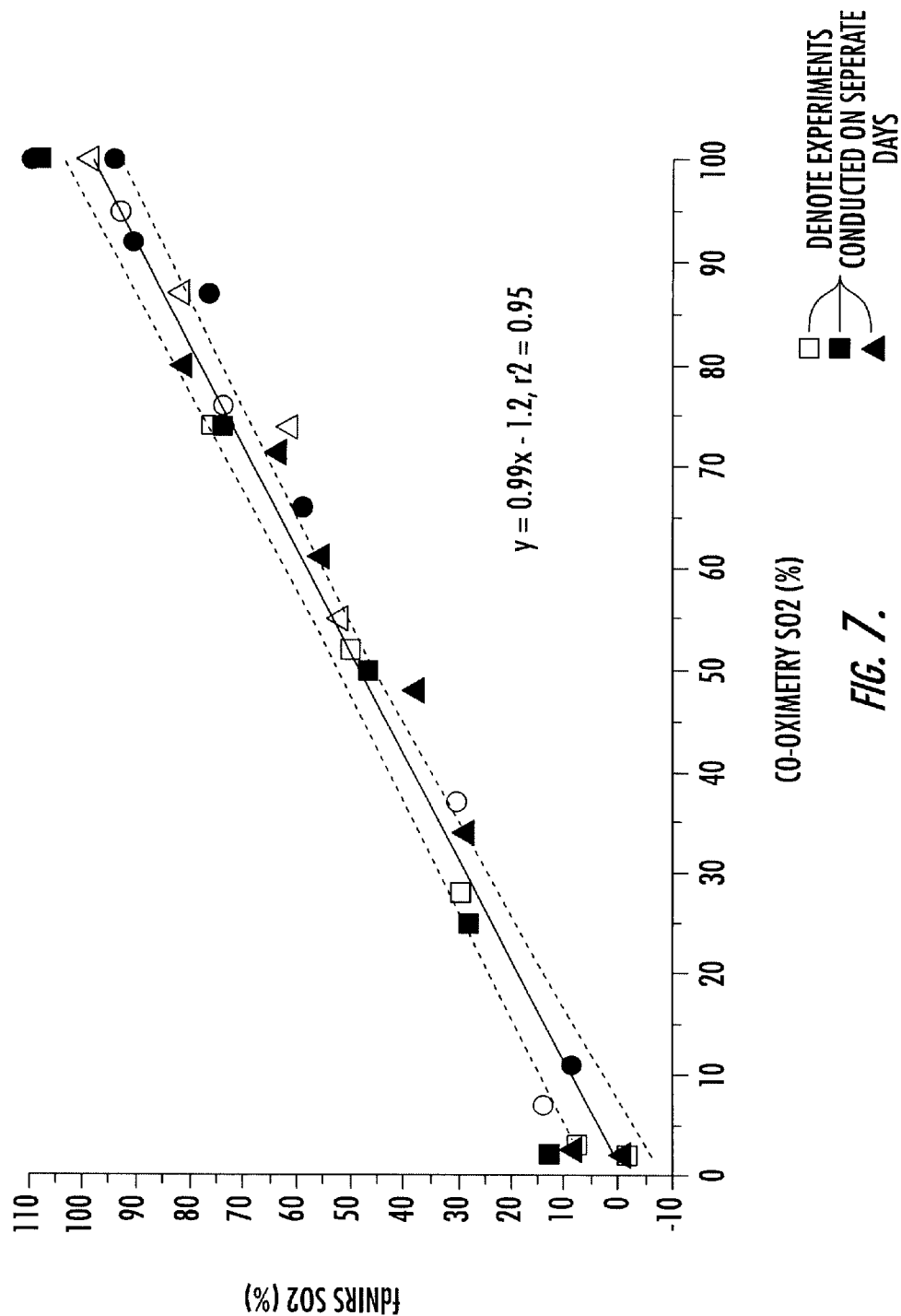
FIG. 7 is a graph of oxygen saturation ($SO_2$) vs. phase difference ratio showing the linear relationship between detected and co-oximetry levels of oxygenation in accordance with a preferred embodiment of the invention.
Figure 8:
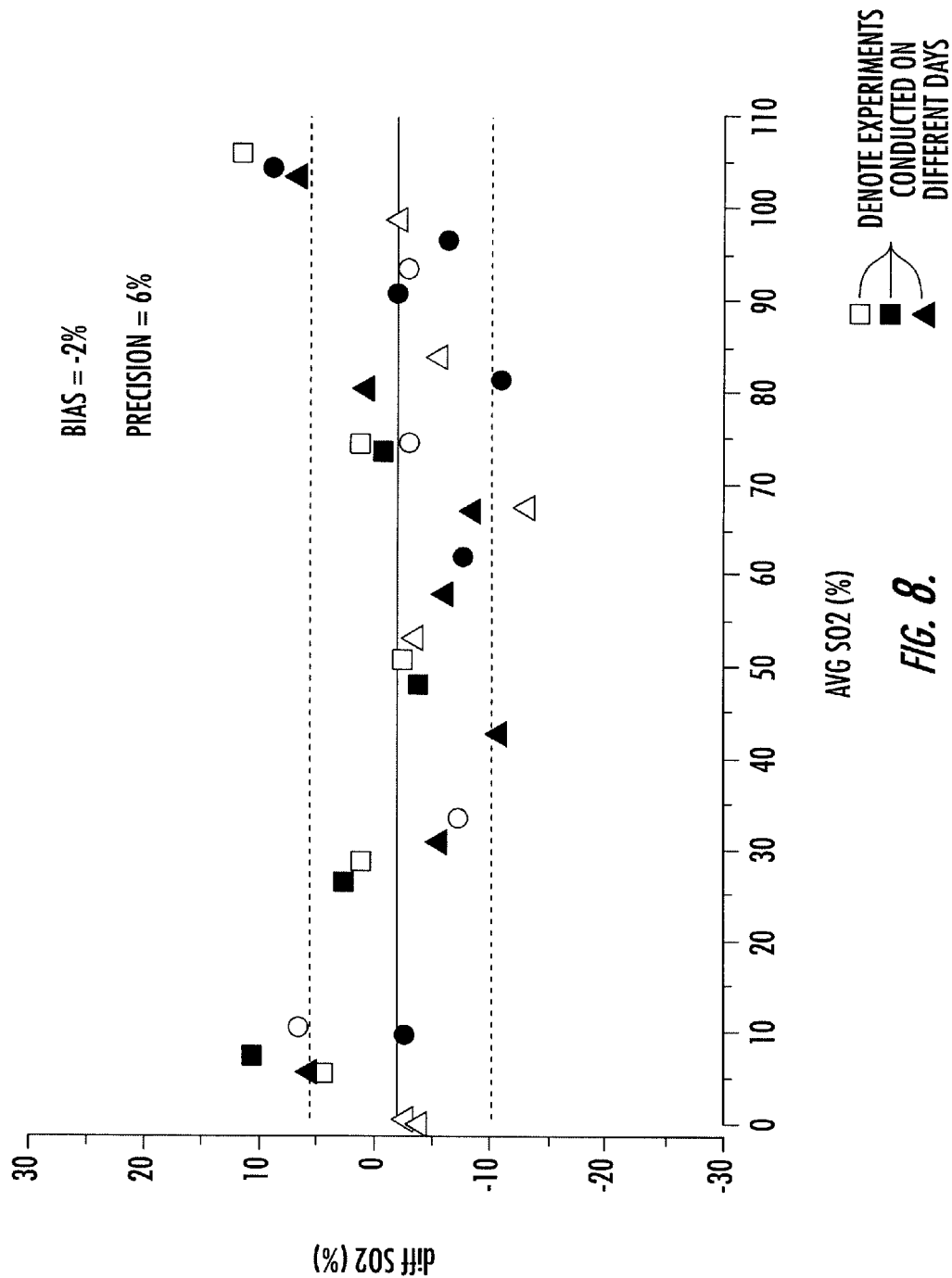
FIG. 8 is a graph of the difference in oxygen saturation (diff. $SO_2$) between detected oxygenation and co-oximetry levels of oxygenation in accordance with a preferred embodiment of the invention.

In the brain model 10, the fdNIRS phase difference ratio was linearly related to perfusate $SO_2$, consistent with equation 19 (FIG. 6). Using this relationship as the fdNIRS $SO_2$ algorithm, linearity was observed between fdNIRS $SO_2$ and CO-Oximeter $SO_2$ in 6 subsequent experiments (FIG. 4, FIG. 7). The line between the variables was not significantly different from the line of identity for any experiment or the combined analysis. fdNIRS $SO_2$ bias and precision were 2% and 6%, respectively (FIG. 8).

The phantom brain was perfused with either deoxygenated or oxygenated blood, achieved by using either $N_2$ or $O_2$, respectively, flowing through the oxygenator. fdNIRS $SO_2$ was measured at each oxygenation state 10 times with the optical probe 15 held in constant position against the brain model 10, or with the probe 15 removed from the brain model 10 between each measurement and repositioned.

fdNIRS $SO_2$ values were similar whether the probe 15 was left on the model brain 10 or repositioned between measurements; however, the measurement variance (SD) was significantly less when the probe was left on vs. repositioned (for oxygenated perfusate, as fdNIRS $SO_2$ was 100±1% vs. 98±5% and 2±1% vs. 6±6% for the oxygenated and deoxygenated perfusate.

Figure 9:
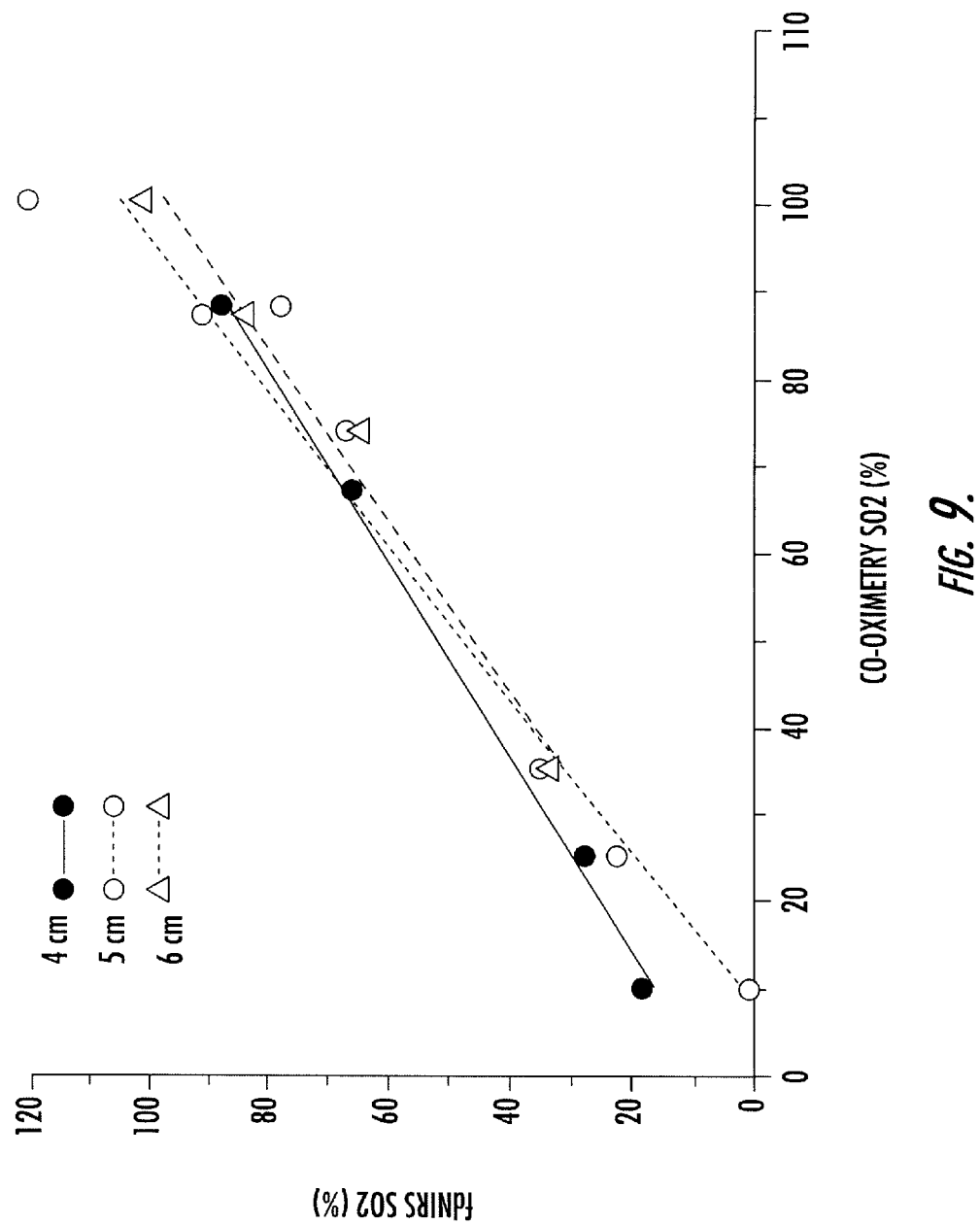
FIG. 9 is a graph of detected oxygenation levels vs. varying source-detector separations in accordance with a preferred embodiment of the invention.
Figure 10:
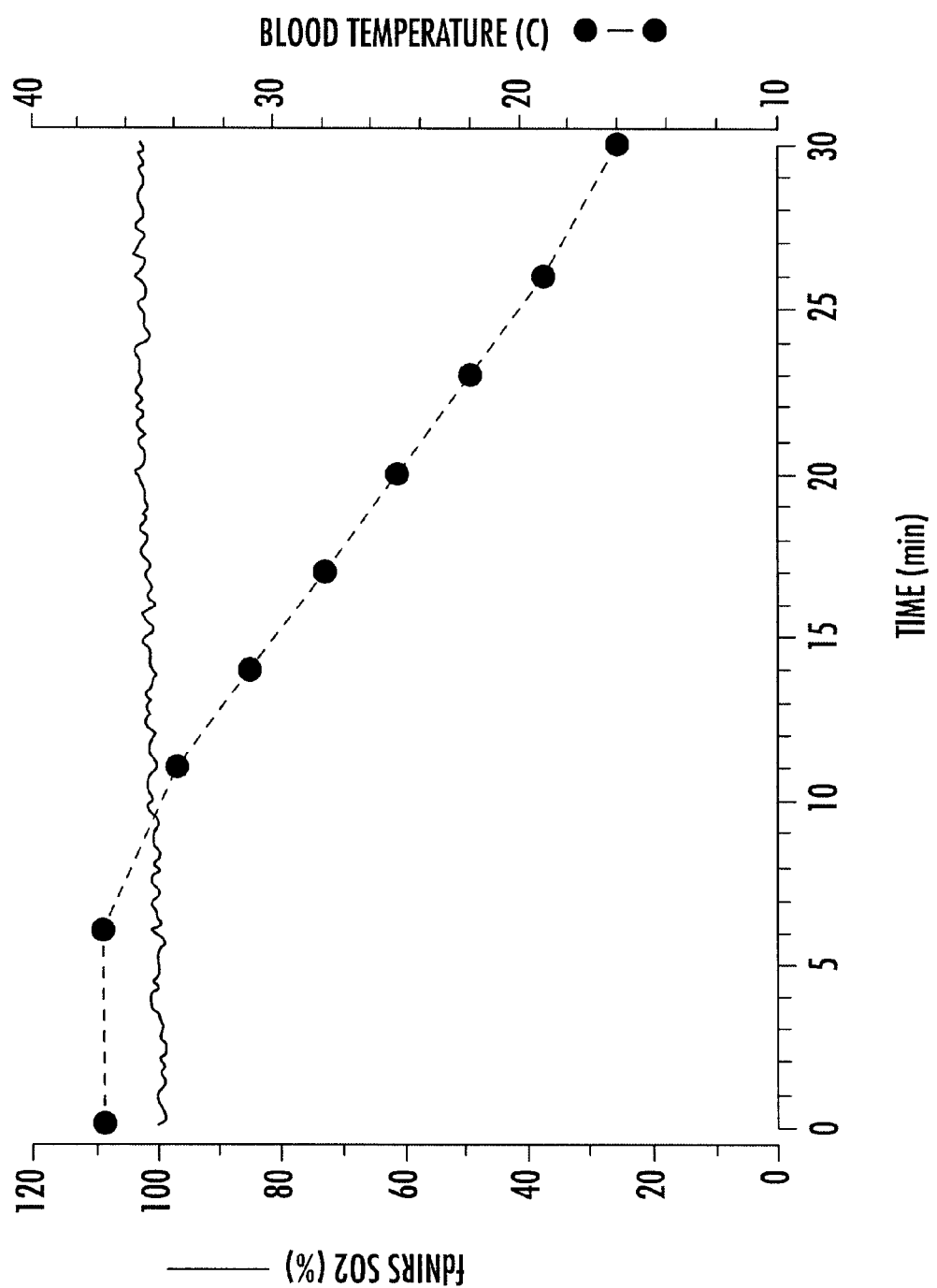
FIG. 10 is a graph of detected oxygen saturation vs. blood temperature in accordance with a preferred embodiment of the invention.
Figure 11:
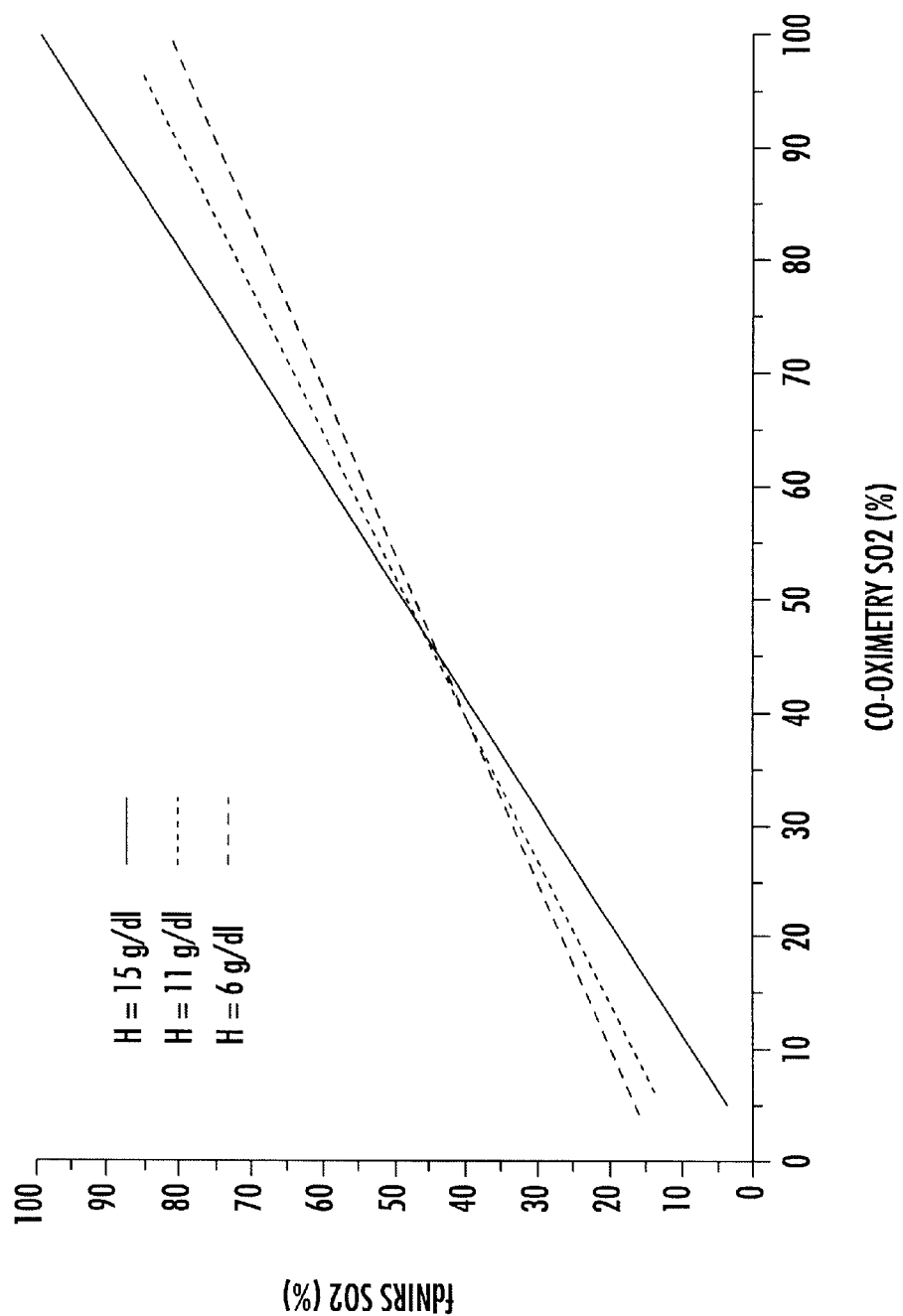
FIG. 11 is a graph of a co-oximetry level as compared to hemoglobin concentration vs. detected oxygenation in accordance with a preferred embodiment of the invention.

The flows of $N_2$ or $O_2$ to the oxygenator are adjusted to achieve 5 levels of perfusate $SO_2$ as measured by CO-Oximetry: 0–10%, 20–35%, 45–60%, 70–85%, and 95–100%. At each level, fdNIRS $SO_2$'s recorded with the source and detector fibers in the probe 15 separated by 4 cm and 5 cm for one experiment, and 5 cm and 6 cm for the second experiment. It is not possible to measure fdNIRS $SO_2$ at 4, 5 and 6 cm for all perfusate $SO_2$ levels during one experiment because of time constraints associated with hemolysis in the brain model 10.

fdNIRS $SO_2$ was measured with emitter-detector separations of 4 cm, 5 cm, and 6 cm as perfusate $SO_2$ was varied (FIG. 9). Linear relationships were observed at each separation, and the lines had similar slopes and intercepts (p=0.27), indicating that source-detector separation did not affect fdNIRS measurement of $SO_2$.

The brain model perfusate $SO_2$ and total hemoglobin concentration are held constant (100%, 15 g/dl) during the experiment. fdNIRS $SO_2$ was recorded as temperature of the perfusate was decreased from 37° C. to 16° C. over 30 minutes.

With oxygenated blood perfusing the brain model 10, fdNIRS $SO_2$ remained unchanged as temperature was decreased from 37° C. to 16° C. (FIG. 5), demonstrating that blood temperature did not affect fdNIRS.

At perfusate total hemoglobin concentrations of 15 g/dl, 10 g/dl, or 6 g/dl, fdNIRS $SO_2$ are recorded as perfusate $SO_2$ in the brain model 10 is varied from 0% to 100%. Experiments with the different hemoglobin concentration are performed on separate days, selected at random.

Linear relationships were observed between fdNIRS $SO_2$ and CO-Oximeter $SO_2$ at each perfusate hemoglobin concentration. (FIG. 6). However, as hemoglobin concentration decreased, slope decreased and intercept increased significantly. Thus, at the lowest hemoglobin concentration and highest oxygenation, fdNIRS $SO_2$ measured −20% low; at the lowest hemoglobin concentration and lowest oxygenation, fdNIRS $SO_2$ measured −10% high.

Thus, hemoglobin concentration influenced oximeter accuracy at very low and high saturation. fdNIRS oximetry errors associated with hemoglobin concentration are related to modulation frequency. By increasing the modulation frequency, the error at very low saturation can be decreased. According to their calculations, modulation frequencies greater than 500 MHz are required to monitor very low saturation in physiologic hemoglobin concentrations. Increasing our fdNIRS to such a frequency may have eliminated the error at very low and high saturation. However, these high modulation frequencies are not obtainable at reasonable cost with current technology, and clinical utility is unlikely to be affected by a 10–15% error at extreme saturations.

FIG. 5 displays the thickness of the intracranial and extracranial tissues in infants, children, and adults. Thickness of the scalp, skull, and subarachnoid space (CSF) increased significantly from infants to adults. Thickness of cortical gray and white matter, however, did not change significantly with age. In children and adults, the extracranial tissues in the occipital region were thicker than those in the frontal region. In the frontal region, the distance from the skin surface to the cortical surface in infants, children, and adults was, respectively, 4±1 mm 6.6±2 mm, and 10.2±4 mm; upper 95% confidence intervals were 6 mm, 10.6 mm, and 20 mm.

While the brain model 10 is perfused with deoxygenated blood, fdNIRS $SO_2$ is recorded with each shell containing either oxygenated blood or no blood, interposed between the model and the optical probe. The experiment is repeated with the brain model 10 perfused with oxygenated blood and each shell containing either deoxygenated blood or no blood. fdNIRS source and detector were 4 cm apart.

Shell thickness around the brain model 10 significantly altered the accuracy of fdNIRS $SO_2$ (FIG. 12). When the perfusate was oxygenated ($SO_2$ 100%), fdNIRS $SO_2$ decreased 26±3% ($p<0.001$) with the 20 mm shell without blood and 32±6% ($p<0.001$) with the 20 mm shell containing deoxygenated blood. When the perfusate was deoxygenated ($SO_2 \approx 0\%$), fdNIRS $SO_2$ increased 21±7% ($p<0.001$) with the 20 mm shell without blood and 26±3% ($p<0.001$) with the 20 mm shell containing oxygenated blood. The 6 mm and 10 mm shells, with or without blood, had no significant effect on fdNIRS $SO_2$. Thus, infant and child simulated extracranial tissues did not affect fdNIRS, whereas the adult simulated extracranial tissue created significant error.

Data were analyzed by least squares linear regression analysis, analysis of variance, or analysis of co-variance. Bias and precision were defined as the mean and SD of, respectively, the ordinate for the difference between fdNIRS and Co-oximeter SO2 vs. the average of fdNIRS and CO-Oximeter SO2. Significance was defined as $p<0.05$.

Thus, the fdNIRS oximeter of the present invention accurately measures $SO_2$ of tissue. The fdNIRS oximeter had excellent linear correlation, bias, and precision relative to CO-Oximetry, a standard method to measure $SO_2$. The fdNIRS oximeter is not influenced by source-detector separation or blood temperature. However, low blood hemoglobin concentration and thick layers overlying the brain model influenced accuracy, suggesting that errors can occur with respect to anemic or adult patients.

It will be appreciated by those skilled in the art that changes could be made to the embodiments described above without departing from the broad inventive concept thereof.

For example, while the methods described herein relate to analysis of the oxygenation of cerebral tissue, the methods described are broadly applicable for determining the oxygenation level of any tissue. It is understood, therefore, that this invention is not limited to the particular embodiments disclosed, but it is intended to cover modifications within the spirit and scope of the present invention.

I claim:

1. A method of determining an oxygenation level of tissue comprising:

providing light signals of a single frequency at at least three separate wavelengths from a near infrared light source to the tissue;

collecting the light signals passing through the tissue with a light detector, the collected signals defining a first, a second and a third light signal; and determining phase differences between the collected light signals defining said first, said second and said third light signal and a reference near infrared light signal and using phase differences to calculate the oxygenation level of the tissue.

2. The method of claim 1 wherein one of the at least three separate wavelengths is less than 800 nm.

3. The method of claim 2 wherein another one of the at least three separate wavelengths is more than 800 nm.

4. A method of determining oxygenation level of tissue comprising:

providing light signals of a single frequency at three separate wavelengths from a near infrared light source to the tissue;

collecting light signals passing through the tissue with a light detector, the collected signals defining a first, a second, and a third light signal having respective wavelengths $\lambda 1$, $\lambda 2$, and $\lambda 3$;

comparing the collected light signals with a reference near infrared signal;

determining a difference in phase between the first and third collected signals $\theta(\lambda 1 - \lambda 3)$;

determining a difference in phase between the second and third collected signals $\theta(\lambda 2 - \lambda 3)$ to define a phase difference ratio of $\theta(\lambda 1 - \lambda 3)/\theta(\lambda 2 - \lambda 3)$; and deriving the oxygenation level of the tissue from the phase difference ratio.

5. The method of claim 4 wherein the first light signal has a wavelength ($\lambda 1$) of less than 800 nm.

6. The method of claim 5 wherein the second light signal has a wavelength ($\lambda 2$) of less than 800 nm and greater than that of ($\lambda 1$).

7. The method of claim 6 wherein the third light signal has a wavelength ($\lambda 3$) of greater than 800 nm.

* * * * *